United States Patent [19]
Avinash et al.

[11] Patent Number: 5,832,134
[45] Date of Patent: Nov. 3, 1998

[54] DATA VISUALIZATION ENHANCEMENT THROUGH REMOVAL OF DOMINATING STRUCTURES

[75] Inventors: Gopal Biligeri Avinash, New Berlin, Wis.; Abdalmajeid Musa Alyassin, Albany, N.Y.

[73] Assignee: General Electric Company, Schenectady, N.Y.

[21] Appl. No.: 757,181

[22] Filed: Nov. 27, 1996

[51] Int. Cl.$^6$ .............................. G06T 5/30; G06K 9/46; G06K 9/54; G06K 9/56

[52] U.S. Cl. ...................... 382/257; 382/262; 382/274; 382/300; 382/131

[58] Field of Search .................... 382/257, 256, 382/260, 262, 274, 300, 299, 131, 132, 128

[56] References Cited

U.S. PATENT DOCUMENTS 5,528,703   6/1996   Lee .......................................... 382/257

OTHER PUBLICATIONS

"Three Dimensional Segmentation of MR Images of the Head Using Probability and Connectivity" by H.E. Cline, W.E. Lorensen, R. Kikinis, F. Jolesz, Journal of Computer Assisted Tomography, vol. 14, No. 6, 1037–1045 (1990).
"Semi–Automated Editing of Computed Tomography Sections for Visualization of Vasculature" by S. Shiffman, G. Rubin, and S. Napel, SPIE 2707: 140–151, (1996).
"Warped Matching for Digital Subtraction of CT–Angiography Studies" by A. Bani–Hashemi, A. Krishnan, and S. Samaddar, SPIE 2710: 428–437, (1996).

*Primary Examiner*—Scott Rogers
*Attorney, Agent, or Firm*—Lawrence P. Zale; Marvin Snyder

[57] ABSTRACT

The present invention provides a system for performing fast segmentation and image processing for enhanced three dimensional (3-D) visualization of a subject. The present invention automatically extracts unwanted dominant features from images while preserving the desired information. The present invention works especially well with Computed Tomography Angiograms (CTA) for viewing vasculature of a subject's head. Segmenting and removing dominant structures from image data permits visualization techniques such as maximum intensity projection (MIP), surface rendering and volume rendering, to provide enhanced vessel visualization.

4 Claims, 5 Drawing Sheets

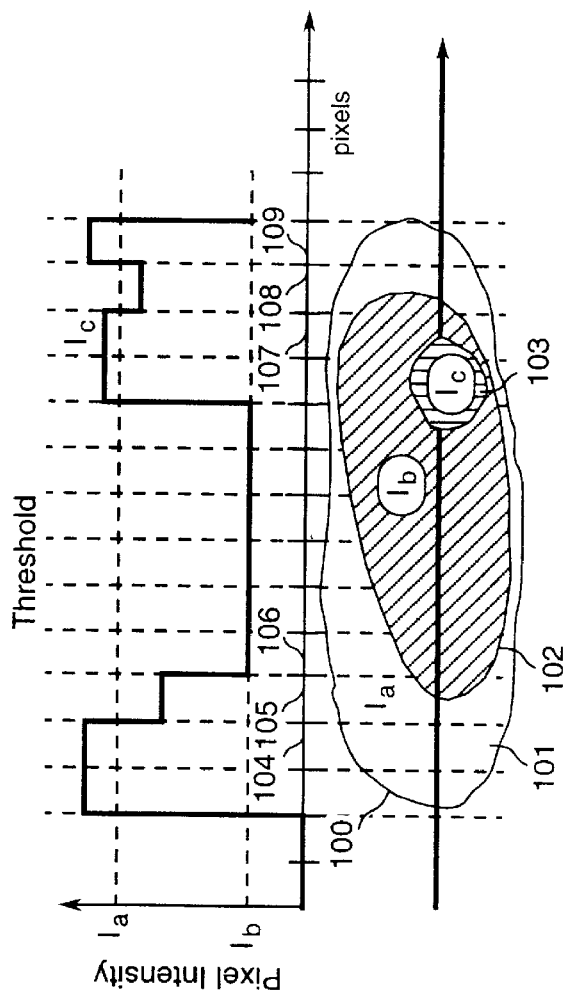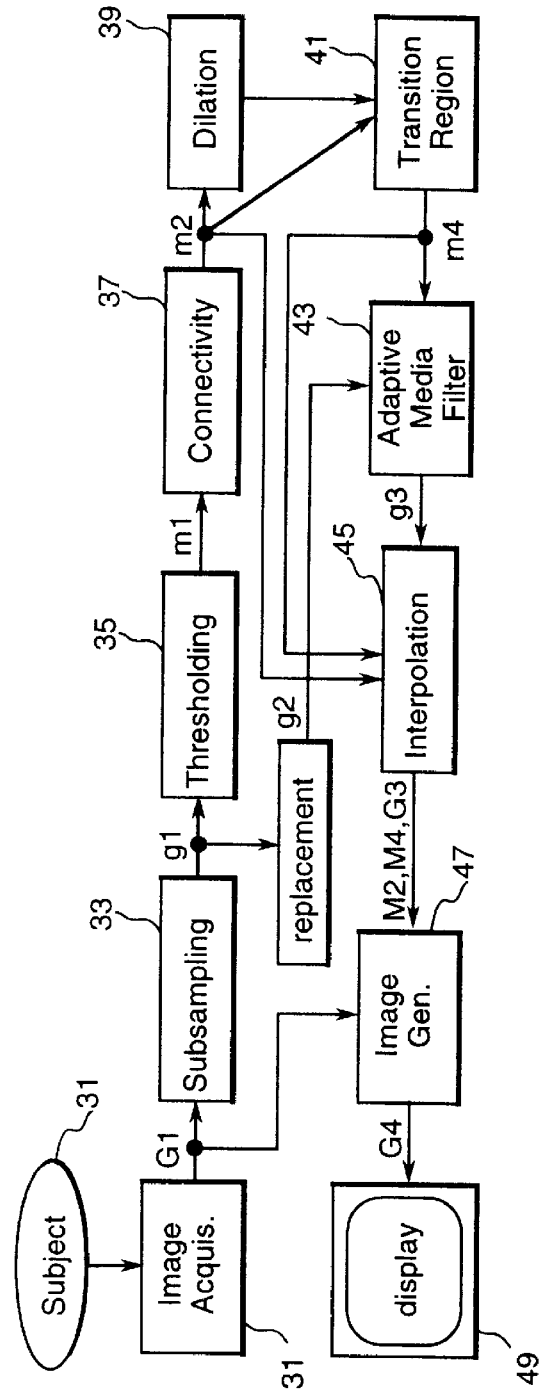

DATA VISUALIZATION ENHANCEMENT THROUGH REMOVAL OF DOMINATING STRUCTURES

BACKGROUND OF THE INVENTION

1. Scope of the Invention

The present invention relates to digital image processing, and more specifically to data visualization enhancement through removal of dominating structures.

2. Related Prior Art

In imaging, a dominant structure, one which provides a large intensity signal, may often mask other less dominant structures desired to be viewed. In maximum intensity projection (MIP) image reconstruction techniques, this becomes very important. MIP reconstructs images by passing imaginary rays through a data volume to an image plane, and uses the largest value intersected as a pixel intensity on the image plane. In most cases this will be the dominant feature, with little, or no representation from the desired structures.

Also, the dynamic range of the intensities causes contrast between desired structures to be small relative to the intensity scale of the image It is highly desirable to remove the dominant structures to enhance the contrast between desired structures relative to the localized region being viewed.

For example, Computed Tomography (CT) is known to provide high contrast between bony structure and soft tissue (e.g. skull and Brain). This high contrast is useful in many medical applications. In Computed Tomography Angiography (CTA) data, however, high intensity bone causes difficulty in extracting 3-D vessels information. This is due to the overlapping intensity distributions of bone and contrast filled vessels.

Current techniques employ semi-automatic tracing to eliminate dominant structures, such as bone. An operator traces regions selected for removal, or alternatively, they trace regions selected for inclusion. A conventional connectivity algorithm, such as that described in "Three Dimensional Segmentation Of MR Images Of The Head Using Probability And Connectivity" by H. E. Cline, W. E. Lorensen, R. Kikinis, F. Jolesz, *Journal of Computer Assisted Tomography*, Vol. 14, No. 6, 1037–1045 (1990), is then used to segment the bone. These approaches may introduce distortion of information when the connectivity algorithm uses a threshold which is too low to exclude bones physically touching the vessels. Such editing also requires a lot of operator time (15–30 minutes). In most cases, the results are influenced by experience and the personal bias of individual operators.

In an effort to reduce the operator time, investigators have developed hybrid semi-automated editing programs described in "Semi-Automated Editing Of Computed Tomography Sections For Visualization Of Vasculature" by S. Shiffman, G. Rubin, and S. Napel, SPIE 2707: 140–151, (1996). In these techniques, an automated 2D segmentation procedure is performed to produce a set of labeled images with each segment associated with a distinct label. Then the user views a small number of labeled images and selects segments of interest by pointing and clicking with a mouse. This activity triggers a connectivity algorithm that collects related segments with similar labels. Selected segments are then used as a mask to extract the corresponding voxel intensities from the raw images. This method is computationally very intensive and currently is not suited in a clinical practice.

Another approach proposed in literature involves the use of warped matching for digital subtraction of data sets corresponding to pre- and post-contrast injection described in "Warped Matching for Digital Subtraction of CT-Angiography Studies" by A. Bani-Hashemi, A. Krishnan, and S. Samaddar, SPIE 2710: 428–437, (1996). This method not only requires the availability of two data sets, which increases the radiation dose to subjects, but is computationally too involved to be of use in routine clinical practice.

Currently there is a need for a system which removes dominating structures for enhancing visualization of desired structures which is clinically feasible.

SUMMARY OF THE INVENTION

A system for enhancing image data $G1(x,y,z)$ by eliminating dominant structures employs a subsampling device for subsampling original image data $G1$ into lower resolution data $g1(x,y,z)$. This enables the invention to speed up processing.

A thresholding device creates a threshold mask $m1(x,y,z)$ being '1' where values of $g1$ are above the threshold, and zero when they are not. This identifies possible locations where the dominating structure would be.

A connectivity device determines connected regions of mask $m1$ as mask $m2$. Non-connected structures are not included in mask $m2$.

A dilation device dilates mask $m2$ by a predetermined amount to create a dilated mask $m3(x,y,z)$.

A transition region device determines a transition region $m4(x,y,z)$ being the difference between dilated mask $m3$ and connected mask $m2$. This indicates pixels which are partially dominant structure and part some other material.

A replacement device calculates an average pixel intensity $\mu$, and creates a replaced data set $g2(x,y,z)$ having value $\mu$ replacing values of $g1$ where the dominant feature was (where $m2=1$), with all other locations being unchanged.

A filter, preferably an adaptive median filter, replaces data values in the transition region defined by $m4$ with filtered values of $g2$ to create transition region replacement data $g3(x,y,z)$ according to:

$$g3(x,y,z) = \begin{cases} \text{filter}(g2(x,y,z)) & \text{if } m4(x,y,z) = 1 \\ g2(x,y,z) & \text{if } m4(x,y,z) = 0; \end{cases}$$

An interpolation device then interpolates $m2$, $m4$, $g3$ into $M2$, $M4$, $G3$ of original resolution, respectively.

An image generator assembles enhanced image data $G4(x,y,z)$ according to:

$$G4(x,y,z) = \begin{cases} \mu & \text{if } M2(x,y,z) = 1 \\ G3(x,y,z) & \text{if } M4(x,y,z) = 1 \\ G1(x,y,z) & \text{otherwise.} \end{cases}$$

The enhanced image data $G4$ is displayed on a display device to produce an enhanced image, having the same resolution of the original image data, without the dominating structure.

OBJECTS OF THE INVENTION

An object of the present invention is to provide a system which removes unwanted dominating structures from an image to produce enhanced images of desired structures.

It is another object of the present invention to provide a system which more clearly images structures with small intensity differences near dominating structures having large image values.

It is another object of the present invention to remove unwanted dominant structures from an image while preserving other structures having approximately the same pixel intensities.

It is another object of the present invention to provide a system which more clearly images vascular structures of a subject even when surrounded by bone.

BRIEF DESCRIPTION OF THE DRAWINGS

The features of the invention believed to be novel are set forth with particularity in the appended claims. The invention itself, however, both as to organization and method of operation, together with further objects and advantages thereof, may be best understood by reference to the following description taken in conjunction with the accompanying drawing in which:

FIG. 1 is an illustration of variation of pixel intensities through a section of a subject.

FIG. 4 is a simplified block diagram of an embodiment of the present invention.

DETAILED DESCRIPTION OF THE INVENTION

Structures within images are sometimes obscured by unwanted dominant structures having exceptionally large data values compared to the remainder of the image. This is especially true in maximum intensity projection (MIP) image reconstruction in which the largest value along a ray passing through a image data volume to an image plane is used as the pixel intensity.

In another case, an unwanted structure may have an image data value range which is similar to, or overlapping data value ranges of other desired structures. In these cases it is desirable to completely define (segment), and remove, the unwanted structures.

In FIG. 1 a sectional image 100 of a subject is shown. Region 101 shows up as intensity $I_a$ in this type of image. Region 102, has intensity $I_b$, and region 103, intensity $I_c$. As one follows ray D through the regions, intensity value are allocated to each pixel, which are denoted with the tick marks, and shown in the graph of FIG. 1. Pixels which are entirely within one region are easy to classify and segment into a particular type of material. However, there are transition pixels, such as 105, 108, which span two regions and are difficult to classify. These are transition regions and cause difficulty in segmentation.

Also note that by simple thresholding with the threshold shown as a dashed line on FIG. 1, region 103 having an intensity of $I_c$, is very similar to region 101 having intensity of $I_a$, and is confused as being a part of structure which is in region 101.

For sake of clarity, the present invention is explained here in terms of Computed Tomography Angiograms (CTA) but may be applied to many different image data sets.

The present invention operates an image data to remove dominating structures, such as connected bone, from the image data set while preserving other desirable structures such as vessel data and calcifications.

Image Data Acquisition

To visualize vessels, a contrast agent is necessary to increase the intensity value of vessels which clearly enhances contrast with surrounding tissues.

Figure 2:
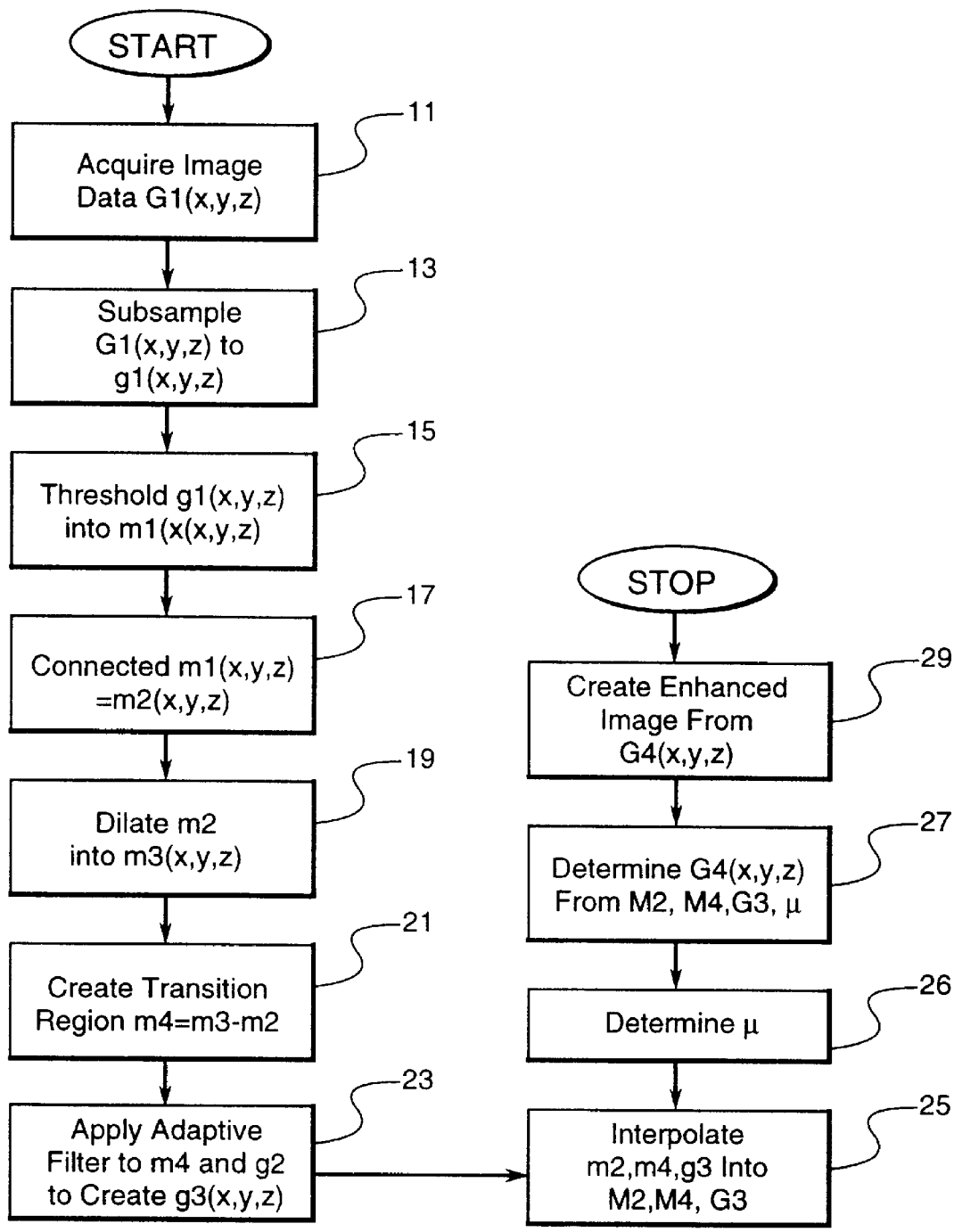
FIG. 2 is a flowchart illustrating the functioning of the present invention.

In FIG. 2 a flowchart is shown illustrating the major steps of the functioning of the present invention.

Image data is acquired in step 11 of FIG. 2. Image data is represented as G1(x,y,z) where (x,y,z) represents a voxel location in a 3D data set and G1 represents the intensity value at (x,y,z) location.

Figure 3A:
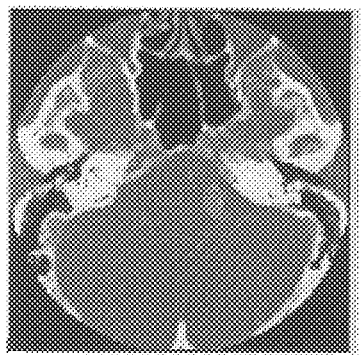
FIG. 3a–3e are illustrations of the result at various points during processing according to the present invention.

In the following explanation, the image data sets were chosen to be CTA, acquired with typical values of x and y spatial resolution being 512×512 and the aspect ratio ranging from 1:1:2 to 1:1:4. The number of slices (z coordinate) covers the volume of interest. An axial CTA image is seen in FIG. 3a.

Data Subsampling

Image data G1(x,y,z) is subsampled in step 13 to a lower x and y spatial resolution of 128×128. The data at lower resolution is referred to with lower case, as g1(x,y,z). Subsampled data sets were isotropic where the aspect ratio was 1:1:1. A 4×4×1 volume of interest (VOI) in G1(x,y,z) data set corresponded to a one voxel in g1(x,y,z) data set. The maximum voxel intensity value of the VOI was used to represent the voxel intensity value at the lower resolution.

Subsampling is used to speed up processing of the data making the present invention clinically feasible.

Threshold Mask

A mask m1(x,y,z) is generated in step 15 for the dominating structure (bone) using a threshold t1 according to:

$$m1(x,y,z) = \begin{cases} 1 & \text{if } g1(x,y,z) > t1 \\ 0 & \text{otherwise.} \end{cases}$$

where (x,y,z) is a location in the subsampled space r.

Figure 3B:

The voxel intensity value of t1 ranged from 1350 to 1500 (Hounsfield number of 350 to 500, and resulted in mask m1 as shown in FIG. 3b.

Step 13 basically retains any voxel having intensity value higher than t1. Although t1 is high enough to contain mainly bone but generally some calcifications are included in the mask. Depending on the size of the calcification and its density, calcification intensity value may reach the bone intensity range value.

Connectivity

In step 17, locations within mask m1(x,y,z) are checked to determine connectivity. Connected high intensity regions are placed in a new mask m2(x,y,z), and high intensity regions such as calcifications, are not.

$$m2(x,y,z) = \text{Connect}(m1(x,y,z))$$

Figure 3C:
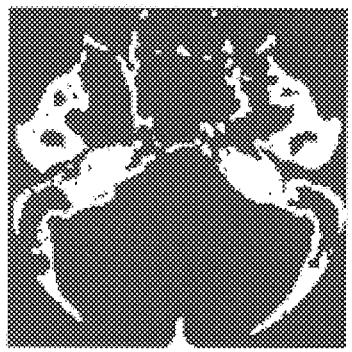

Mask m1(x,y,z) is analyzed to remove non-bone tissue and to retain only connected bone in mask m2(x,y,z) as shown in FIG. 3c. Since calcifications are generally located internal to the vessels, calcifications will not be included in the mask m2(x,y,z).

Dilation Mask

Another mask m3(x,y,z) is generated in step 19 by dilating m2(x,y,z) by a predetermined number of pixels in each dimension, for example, a 3×3×3 dilation (3 pixels for each dimension) was used, according to:

$$m3(x,y,z) = \text{Dilate}(m2(x,y,z))$$

Figure 3D:
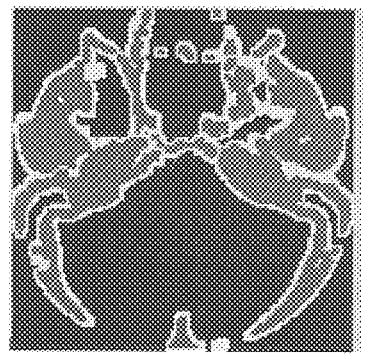

Mask m3 is shown in FIG. 3d.

Dilation of the mask expands the connected marked bone. The 3×3×3 size kernel corresponds to a kernel size of 12×12×12 at original data size. This will involve any volume that was not included in the original mask.

Transition Volume Mask

A transition mask m4(x,y,z) is created in step 21 using m2(x,y,z) as follows:

$$m4(x,y,z) = m3(x,y,z) - m2(x,y,z).$$

Figure 3E:
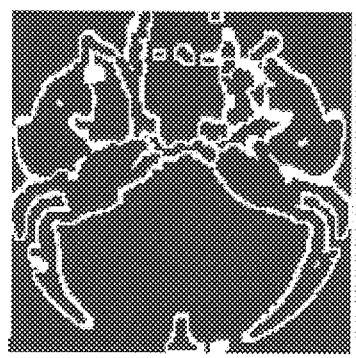

Mask m4 is shown in FIG. 3e. Note now transition mask m4(x,y,z) marks the volume of bone that has intensity value lower than the threshold t1 that was absent from mask m1.

Dominant Feature Replacement

Vessel data g2(x,y,z) is generated using g1(x,y,z) and m2(x,y,z) mask as shown below:

$$g2(x,y,z) = \begin{cases} g1(x,y,z) & \text{if } m2(x,y,z) = 0 \\ \mu & \text{if } m2(x,y,z) = 1 \end{cases}$$

where $\mu$ is the vessel surrounding tissue mean intensity value. In the present example, it was $\mu=1050$. Note that g2(x,y,z) still contains bone of intensity value lower than t1 which is mainly due to partial volume averaging. Also note that thresholding generates sharp edges between where high intensity bone used to be, and low intensity bone.

Adaptive Filter

Transition regions defined by mask m4(x,y,z) are replaced by filtered values in step 23 to result in a filtered data set g3. One preferred embodiment is to use adaptive median filtering as shown below:

$$g3(x,y,z) = \begin{cases} \text{median}(g2(x,y,z)) & \text{if } m4(x,y,z) = 1 \\ g2(x,y,z) & \text{if } m4(x,y,z) = 0. \end{cases}$$

For example, a 3×3×3 transition mask 3×3×3 kernel may be used. If the kernel's center voxel passes over the transition region, then the median voxel value of the corresponding voxels in g2 would be used in g3.

Median filter is a nonlinear smoothing filter which removes speckles or sharp edges. Low intensity bone is replaced by non bone neighboring voxel values. Note this filter is used only where low intensity bone exists (i.e., where m2(x,y,z)=1).

Other filtering methods may be used. In the adaptive median filtering method above, vessels data is not affected by this filter. Also note that no new data values are generated as in other filters. In other filtering methods, it is best of only original data values are used, replacing others.

Interpolation

Subsampled data g3(x,y,z), and masks m2(x,y,z) and m4(x,y,z) are then interpolated in step 25 to the original spatial resolution 512×512×N to produce G3(x,y,z), M2(x,y,z) and M4(x,y,z), respectively, where N is the original number of slices. There are several conventional interpolation techniques that exist in the literature which may be used. Trilinear interpolation was used for G3(x,y,z) and voxel replication was used for masks M2, M4.

Image Generation

Vessel data G4(x,y,z) is generated as final output in step 27 from M2(x,y,z), M4(x,y,z), G1(x,y,z), and G3(x,y,z) as shown below:

$$G4(x,y,z) = \begin{cases} \mu & \text{if } M2(x,y,z) = 1 \\ G3(x,y,z) & \text{if } M4(x,y,z) = 1 \\ G1(x,y,z) & \text{otherwise;} \end{cases}$$

where R is the original volume data set.

Note G4(x,y,z) data set includes the original vascular data G1(x,y,z) at the same resolution that was acquired. Also it minimally includes processed data where only low intensity bone used to be located.

Implementation

A simplified block diagram of an embodiment of the present invention is shown in FIG. 4.

Image data G1(x,y,z) is acquired of a subject 1 by an image acquisition device 31.

Image data G1 is subsampled to a lower x and y spatial resolution g1(x,y,z), for example, 128×128, by a subsampling device 33 coupled to image acquisition device 31.

A thresholding device 35 receives the lower resolution image data g1 and generates a mask m1(x,y,z) for the dominating structure (bone) using a threshold t1.

A connectivity device 37 reads mask m1 (x,y,z) from thresholding device 35 and determines which of the locations of m1 are connected. These are stored in mask m2(x,y,z).

A dilation device 39 coupled to connectivity device 37, dilates mask m2 by a predetermined number of pixels in each dimension, for example, a 3×3×3 dilation, to produce another mask m3(x,y,z).

A transition region device 41 is coupled to dilation device 39 and connectivity device 37 and receives masks m3, m2 from them, respectively. Transition region device subtracts m2 form m3 to result in a transition mask m4(x,y,z).

A replacement device 42, receives the subsampled data g1 from subsampling device 33, and creates an average $\mu$ of the pixel intensities. It then creates a replaced data set g2(x,y,z) having value $\mu$ replacing values of g1 where the dominant feature was, with all other locations being unchanged to result in data g2(x,y,z).

An adaptive median filter 43 receives m4 from transition region device 41, and data g2 from replacement device 42, and replaces values of g2 corresponding locations within the transition region with median values as described in step 23 of FIG. 2 to result in filtered data g3(x,y,z).

An interpolation device 45 receives filtered data g3(x,y,z), masks m2(x,y,z), m4(x,y,z) and then interpolated these to the original spatial resolution 512×512×N to produce G3(x,y,z), M2(x,y,z), M4(x,y,z), respectively, where N is the original number of slices.

An image generation device 47 receives M2(x,y,z), M4(x,y,z), and G3(x,y,z) from interpolation device 45, and original data G1 from image acquisition device 31 and generates final image data G4. It assembles final image data G4 using the value $\mu$ for locations where the dominant feature filled the entire pixel, identified by mask M2. It uses values G3 in transition area identified by mask M4, and uses original data values G1 unchanged for all other locations.

Results

Figure 5A:
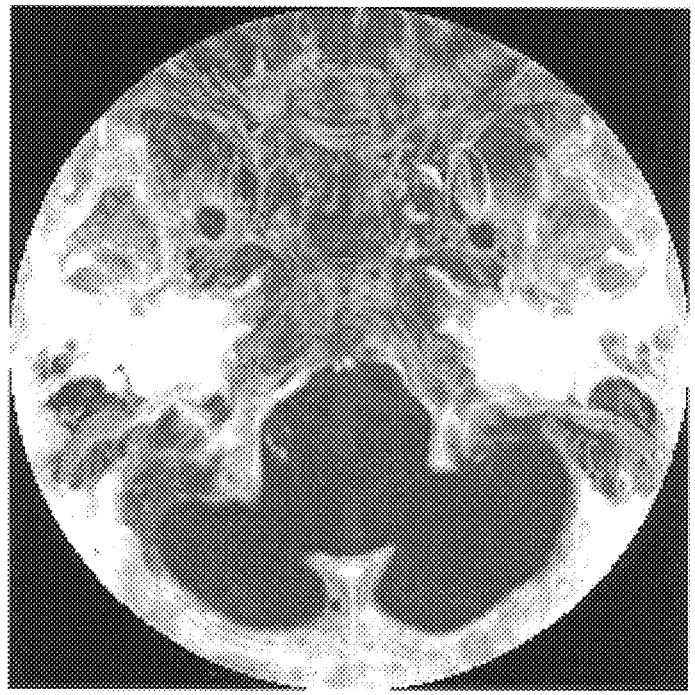
FIG. 5a is a maximum intensity projection (MIP) image of a first Computed Tomography Angiography (CTA) data set.
Figure 5B:
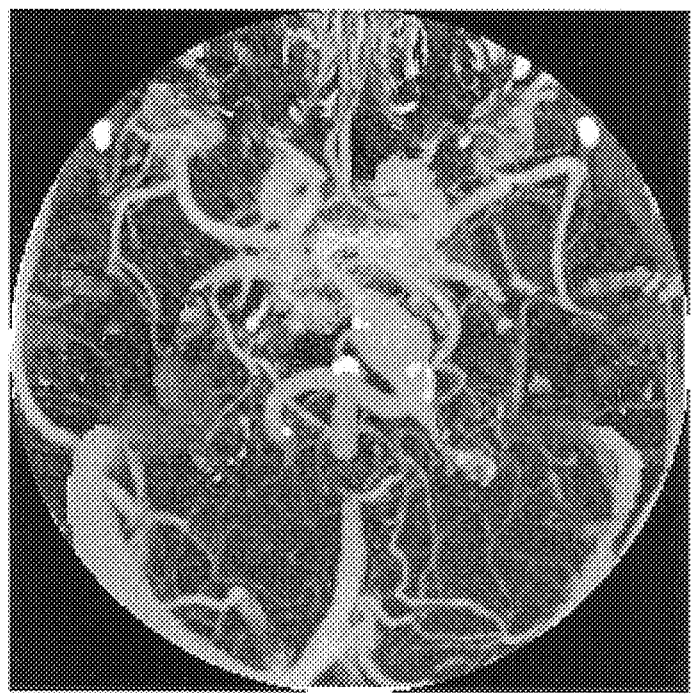
FIG. 5b is MIP of the data set used in FIG. 5a after employing the present invention.

FIG. 5a shows an MIP image of a conventional CTA data set. FIG. 5b is the image created by MIP after the image data set of FIG. 5a has been processed according to the present invention.

Figure 6A:
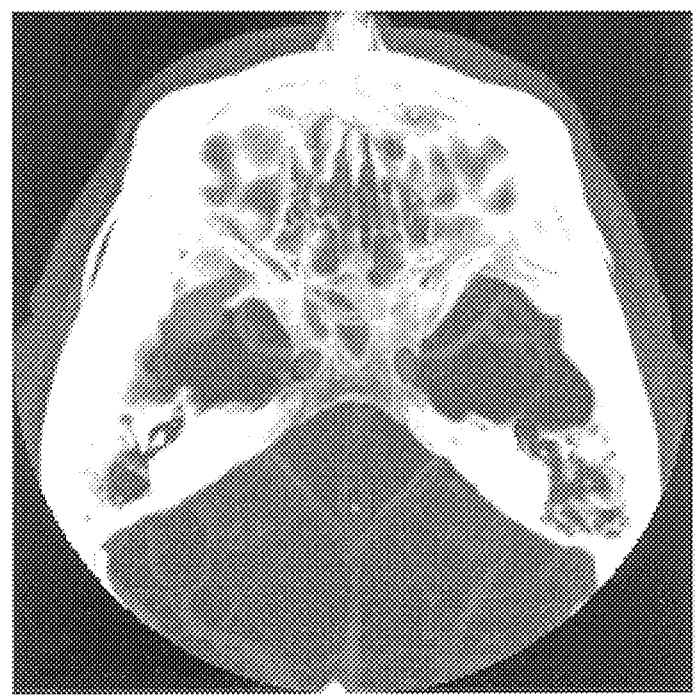
FIG. 6a is an MIP image of a second CTA data set.
Figure 6B:
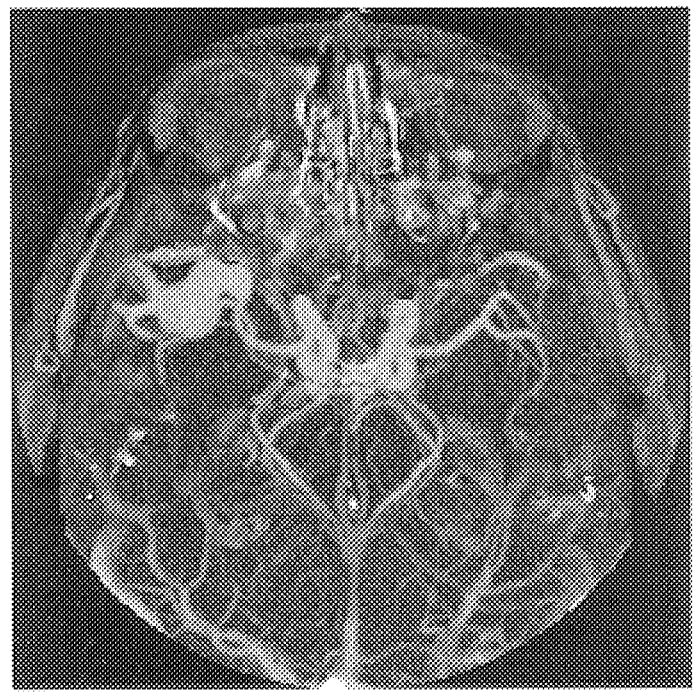
FIG. 6b is MIP of the data set used in FIG. 6a after employing the present invention.

Similarly, FIG. 6a is an MIP image of a conventional CTA data set. FIG. 6b is the image created by MIP after the image data set of FIG. 6a has been processed according to the present invention.

The present invention, applied on 30 MBytes CTA image data, ran under 2 minutes CPU time on a Sun-Sparc 20 computer. For a 512×512×60 data set volume with 16 bit voxel value, it took approximately one minute to segment the data using the proposed technique. Therefore, this technique is clinically feasible and will be an effective tool to aid a clinician in extracting diagnostic information.

While several presently preferred embodiments of the novel invention have been described in detail herein, many modifications and variations will now become apparent to those skilled in the art. It is, therefore, to be understood that the appended claims are intended to cover all such modifications and variations as fall within the true spirit of the invention.

What is claimed is:

1. A method of enhancing image data G1(x,y,z) comprising the steps of:

a) subsampling original image data G1 into lower resolution data g1(x,y,z);

b) thresholding g1 to create a threshold mask m1 with values of m1 being '1' where values of g1 are above the threshold, and zero when they are not;

c) determining connected regions of mask m1 and saving them as mask m2;

d) dilating mask m2 by a predetermined amount to create a dilated mask m3(x,y,z);

e) determining a transition region m4(x,y,z) being the difference between dilated masks m3 and threshold m2;

f) applying a filter to the region defined by m4 to create transition region replacement data g3(x,y,z);

g) interpolating m2, m4, g3 into M2, M4, G3 of original resolution, respectively;

h) determining a mean pixel intensity $\mu$ from the image data G1;

i) assembling image data G4(x,y,z) according to:

$$G4(x,y,z) = \begin{cases} \mu & \text{if } M2(x,y,z) = 1 \\ G3(x,y,z) & \text{if } M4(x,y,z) = 1 \\ G1(x,y,z) & \text{otherwise; and} \end{cases}$$

j) displaying image data G4 as an enhanced image.

2. The method of enhancing images of claim 1 wherein the step of filtering comprises the step of applying an adaptive median filter to the region defined by m4 to create transition region replacement data g3(x,y,z).

3. The system for enhancing image data G1(x,y,z) comprising:

a) a subsampling device for subsampling original image data G1 into lower resolution data g1(x,y,z);

b) a thresholding device coupled to the subsampling device, for thresholding g1 to create a threshold mask m1 with values of m1 being '1' where values of g1 are above the threshold, and zero when they are not;

c) a connectivity device coupled to the thresholding device for receiving mask m1 and for determining connected regions of mask m1 and saving them as mask m2;

d) a dilation device coupled to the connectivity device for dilating mask m2 by a predetermined amount to create a dilated mask m3(x,y,z);

e) a transition region device coupled to the dilation device and the thresholding device for determining a transition region m4(x,y,z) being the difference between dilated masks m3 and threshold m2;

f) a replacement device, coupled to the subsampling device, for creating an average pixel intensity $\mu$, and creating a replaced data set g2(x,y,z) having value $\mu$ replacing values of g1 where the dominant feature was (where m2=1), with all other locations being unchanged;

g) a filter coupled to the transition region device and the replacement device for replacing data values in the region defined by m4 with filtered values of g2 to create transition region replacement data g3(x,y,z) according to:

$$g3(x,y,z) = \begin{cases} \{\text{filter}(g2(x,y,z)) & \text{if } m4(x,y,z) = 1 \\ \{g2(x,y,z) & \text{if } m4(x,y,z) = 0; \end{cases}$$

h) an interpolation device coupled to the filter, dilation, thresholding devices, for interpolating m2, m4, g3 into M2, M4, G3 of original resolution, respectively;

i) an image generator coupled to the interpolation device, for assembling image data G4(x,y,z) according to:

$$G4(x,y,z) = \begin{cases} \mu & \text{if } M2(x,y,z) = 1 \\ G3(x,y,z) & \text{if } M4(x,y,z) = 1 \\ G1(x,y,z) & \text{otherwise; and} \end{cases}$$

j) a display device coupled to the image generation device, for displaying image data G4 as an enhanced image.

4. The system for enhancing images of claim 3 wherein the filter comprises an adaptive median filter which filters data in the region defined by m4 to create transition region replacement data g3(x,y,z).

* * * * *